US006815172B1

(12) United States Patent
Martinez et al.

(10) Patent No.: US 6,815,172 B1
(45) Date of Patent: Nov. 9, 2004

(54) METHODS AND COMPOSITIONS FOR OPSONOPHAGOCYTIC ASSAYS

(75) Inventors: Joseph E. Martinez, Morrow, GA (US); George M. Carlone, Stone Mountain, GA (US); Michael H. Hickey, Oakdale, IL (US); Sandra Steiner, Atlanta, GA (US)

(73) Assignees: The United States of America as represented by the Department of Health and Human Services, Washington, DC (US); Flow Applications, Inc., Okawville, IL (US)

( * ) Notice: Subject to any disclaimer, the term of this patent is extended or adjusted under 35 U.S.C. 154(b) by 0 days.

(21) Appl. No.: 10/009,660

(22) PCT Filed: Jun. 9, 2000

(86) PCT No.: PCT/US00/15858

§ 371 (c)(1),
(2), (4) Date: Dec. 7, 2001

(87) PCT Pub. No.: WO00/77518

PCT Pub. Date: Dec. 21, 2000

Related U.S. Application Data

(60) Provisional application No. 60/138,911, filed on Jun. 11, 1999.

(51) Int. Cl.[7] .......................... C12Q 1/00; G01N 33/53; G01N 33/554; G01N 33/569; G01N 33/537
(52) U.S. Cl. ........................ 435/7.32; 435/4; 435/7.1; 435/7.2; 435/7.32; 435/7.33; 435/7.34; 435/7.35; 435/7.37; 435/7.92; 435/29; 435/34; 435/69.3; 435/332; 435/340; 436/172; 436/501; 436/507; 436/546; 436/800

(58) Field of Search .................... 435/2, 3, 4, 7.1, 435/7.2, 7.21, 7.32, 7.34, 7.9, 7.92, 7.93, 7.94, 7.95, 8.29, 34, 35, 36, 38, 40.51, 41, 69.3, 71.3, 174, 175, 176, 327, 333, 334, 340

(56) References Cited

U.S. PATENT DOCUMENTS

| 5,219,763 A | 6/1993 | Van Hoegaerden |
| 5,405,784 A | 4/1995 | Van Hoegaerden |
| 5,474,905 A | 12/1995 | Tai et al. |
| 5,571,511 A | * 11/1996 | Fischer .................. 424/165.1 |
| 5,747,349 A | 5/1998 | van den Engh et al. |
| 5,855,901 A | 1/1999 | Malcolm |

OTHER PUBLICATIONS

Romero–Steiner et al. 1997. Clin. and Diagnostic Lab. Immuno. 4(4):415–422.*
Sveum et al. J. of Immuno. Meth. 1986. 90:257–264.*
Shyamala et al., "Human–Isotype–Specific Enzyme Immunoassay for Antibodies to Pneumococcal Polysaccharides," J. Clin. Microbiol. 26:1575–1579 (1988).

(List continued on next page.)

*Primary Examiner*—Lynette R. F. Smith
*Assistant Examiner*—Ja-Na Hines
(74) *Attorney, Agent, or Firm*—Klarquist Sparkman, LLP

(57) ABSTRACT

Methods and compositions comprising immunoassays for the detection of functional antibodies and the analysis of vaccine efficacy are described. In particular, the present invention provides opsonophagocytic assays. The assays are useful for the rapid and simultaneous detection of multiple different functional antibodies. In preferred embodiments, the assays include fluorescent labels of multiple colors and/or intensities.

33 Claims, 8 Drawing Sheets

| Method | Serogroup A | | Serogroup C | |
|---|---|---|---|---|
| | Pre (n=35) | Post (n=35) | Pre (n=35) | Post (n=35) |
| SBA | 612 | 10,023 | 46 | 2,649 |
| OP | 412 | 16,712 | 86 | 4,993 |

OTHER PUBLICATIONS

Romero–Steiner et al., "Standardization of an Opsonophagocytic Assay for the Measurement of Functional Antibody Activity against *Streptococcus pneumoniae* Using Differentiated HL–60 Cells," *Clin. Diagn. Lab. Immunol.* 4:415–422 (1997).

Martinez et al., "A Flow Cytometric Opsonophagocytic Assay for Functional Antibody Against *S. pneumoniae*," First International Symposium on Pneumococci and Pneumococcal Diseases held Jun. 13–17, 1998, Helsingor, Denmark. Abstract printed in abstract book distributed at the meeting and poster presented at the meeting.

Database Medline 'Online!, American Medical Association; abstract No. 86252398, 1986, R.J. Sveum et al.: "A Quantitative Fluorescent Method for Measurement of Bacterial Adherence and Phagocytosis." XP002188000.

* cited by examiner

| Method | Serogroup A | | Serogroup C | |
|---|---|---|---|---|
| | Pre (n=35) | Post (n=35) | Pre (n=35) | Post (n=35) |
| SBA | 612 | 10,023 | 46 | 2,649 |
| OP | 412 | 16,712 | 86 | 4,993 |

FIG. 1

Table 2. Competitive inhibition of opsonophagocytic activity of reference sera after absorption with specific serogroup A and C *Neisseria meningitidis* polysaccharide (200 μg/ml)

| CDC reference sera | Serogroup A | | | Serogroup C | | |
|---|---|---|---|---|---|---|
| | Titer Before Absorption | Titer After Absorption | % decrease | Titer Before Absorption | Titer After Absorption | % decrease |
| 205 | 1024 | 4 | 99.6 | 256 | 4 | 98.4 |
| 209 | 1024 | 4 | 99.6 | 4096 | 8 | 99.8 |
| 219 | 1024 | 8 | 99.2 | 512 | 8 | 98.4 |
| 233 | 512 | 4 | 99.2 | 256 | 4 | 98.4 |
| 243 | 256 | 4 | 98.4 | 128 | 4 | 96.8 |
| Mean % decrease | | | 99.2 |

Table 3. Correlations of SBA, OP and ELISA (µg/ml) concentrations (n=70) for *Neisseria meningitidis* serogroups A and C

| Serogroup A | | | Serogroup C | | |
|---|---|---|---|---|---|
| ELISA vs SBA | ELISA vs OP | SBA vs OP | ELISA vs SBA | ELISA vs OP | SBA vs OP |
| r=0.89<br>p <0.01[a] | r=0.83<br>p <0.01 | r=0.75<br>p <0.01 | r=0.85<br>p <0.01 | r=0.74<br>p <0.01 | r=0.79<br>p <0.01 | a. Pearson's correlation

FIG. 3

Table 1. Competitive inhibition of opsonophagocytic activity with type-specific polysaccharide.

| Serotype[a] | Opsonophagocytic activity | | | Average percent inhibition[c] |
|---|---|---|---|---|
| | Median titer | Range | Median titer after | |
| 4 | 2048 | 512 to 2048 | 4 | 99.7 |
| 6B | 128 | 64 to 512 | 4 | 97.0 |
| 9V | 512 | 256 to 2048 | 4 | 99.3 |
| 14 | 512 | 256 to 512 | 4 | 98.9 |
| 18C | 256 | 128 to 512 | 4 | 98.9 |
| 19F | 128 | 64 to 256 | 4 | 96.9 |
| 23F | 128 | 64 to 512 | 4 | 96.9 |

[a]Serotype of *Streptococcus pneumoniae*.

[b]All titers in the presence of 0.5 mg/ml of homologous Ps were <1:8, and were reported as a titer of 4 for analysis purposes.

[c]Percent inhibiton of opsonophagocytic activity after addition of type-specific polysaccharide.

Fig. 6

TABLE 2. Correlation between the flow cytometric and manual viable opsonophagocytic assays for pre- and postvaccination serum.

| Streptococcus pneumoniae serotype | Geometric mean titer | | | | Correlation[a] | | |
|---|---|---|---|---|---|---|---|
| | Flow cytometric | | Manual viable | | r value | P value | Slope |
| | Pre | Post | Pre | Post | | | |
| 4 | 5 | 157 | 5 | 117 | 0.90 | <0.001 | 0.83 |
| 6B | 12 | 176 | 11 | 98 | 0.85 | <0.001 | 0.80 |
| 9V | 5 | 665 | 6 | 256 | 0.88 | <0.001 | 0.70 |
| 14 | 24 | 562 | 24 | 352 | 0.87 | <0.001 | 0.77 |
| 18C | 6 | 83 | 7 | 63 | 0.89 | <0.001 | 0.84 |
| 19F | 7 | 56 | 7 | 53 | 0.95 | <0.001 | 1.01 |
| 23F | 5 | 20 | 5 | 31 | 0.91 | <0.001 | 0.94 |

[a]The Pearson's product moment correlation coefficient was used for the linear regression analysis between the two methods. The overall correlation between the two assays for all serotypes combined was r = 0.89, P < 0.001, and slope = 0.81. Twenty-four paired sera were tested to determine the correlation between the two assays.

Fig. 7

TABLE 3. Cummulative percentage of serum samples (n = 48) analyzed by the flow cytometric opsonophagocytic assay differing in titer as compared with the manual assay.

| Dilution well difference from median manual opsonophagocytosis titer | Streptococcus pneumoniae Serotype | | | | | | | |
|---|---|---|---|---|---|---|---|---|
| | 4 | 6B | 9V | 14 | 18C | 19F | All |
| 0 | 59.4 | 45.3 | 43.8 | 39.1 | 50 | 65.6 | 52 |
| ±1 | 75 | 70.3 | 59.4 | 76.6 | 78.2 | 96.8 | 75.9 |
| ±2 | 87.5 | 84.3 | 75.0 | 89.1 | 87.5 | 98.4 | 87.2 |
| ±3 | 98.5 | 92.1 | 87.5 | 95.4 | 95.3 | 98.4 | 94.6 |

Fig. 8

METHODS AND COMPOSITIONS FOR OPSONOPHAGOCYTIC ASSAYS

CROSS REFERENCE TO RELATED APPLICATIONS

This is the National Stage of International Application No. PCT/US00/15858, filed Jun. 9, 2000, which was published in English under PCT Article 21(2), which claims the benefit of U.S. Provisional Application 60/138,911, filed Jun. 11, 1999.

This invention was made by the Centers for Disease Control and Prevention, an agency of the U.S. Government. Therefore, the U.S. Government has certain rights in this invention.

FIELD OF THE INVENTION

The present invention relates to the field of immunologic detection of functional antibodies.

BACKGROUND OF THE INVENTION

Within the last decade, the emergence of multi-drug resistant pathogens has led to the increased use of vaccines as a method of treating infectious disease. Vaccine development and immunization has moved to the forefront of both international and national concerns as evidenced by the recent establishment of organizations such as the International Vaccine Institute established in 1996, and the Vaccine and Immunization Division of the Pan American Health Organization established in 1999. To date, the United States alone has more than twenty different federal government agencies that play a role in the development of vaccines.

With this increase in importance, new vaccines are being developed at a rapid pace, and assays to determine the in vivo efficacy of these vaccines are also being developed. Several assays have been developed that determine the efficacy of vaccines by detecting vaccine-specific antibodies generated in vivo after vaccine administration. These assays include radioantigen binding assays and enzyme-linked immunosorbant assays (ELISAs) (Schiffman et al., 1980; Nahm et al., 1996; Quataert et al., 1995). One notable problem with these assays, is that they measure the total amount of antibody generated in response to administration of the vaccine without regard to whether the antibodies actually provide a protective response in the immunized individual. Therefore, traditional assays do not provide an accurate picture as to the in vivo efficacy of a vaccine.

Whether a vaccine provides protective immunity or simply generates an antibody response depends upon the type of infection the vaccine seeks to prevent as well as the type of antibodies generated in response to administration of the vaccine. For example, a protective immune response to pathogens such as *Streptococcus pneumoniae* and *Neisseria meningitidis* involves opsonophagocytosis of the infectious agents. Opsonophagocytosis is the binding (or opsonization) of antibodies and complement or complement components to the infectious agent and the subsequent uptake of the infectious agent by effector cells via the binding of the effector cells to the antibody/antigen complex. Therefore, a protective immune response against such pathogens requires more than the mere generation of antibodies that bind the pathogen. A protective immune response requires the generation of "functional" antibodies that bind to the infectious agents and also provide a means for uptake and clearance by effector cells. Another aspect of functionality, is the ability to interact with complement reactions that may also be necessary for opsonphagocytosis.

Since functional antibodies play a major role in the generation of a protective response against infection by certain pathogens, vaccines for these pathogens must also generate functional antibodies in order to protect against infection. Assays that determine the effectiveness of vaccines of this nature should test for the production of functional antibodies. Notably, the Federal Drug Administration has taken this stance with regard to all future pneumococcal vaccines and will require measurement of antibody levels using functional assays which more closely approximate biologic function of the host.

One functional assay that has been developed to measure the efficacy of vaccines is the opsonophagocytic assay. Opsonophagocytic assays are more attractive than other measures of in vitro protective immunity because they more closely resemble animal models, and appear to provide a closer correlation with serotype-specific vaccine efficacy than other prior art assays such as ELISAs (Wenger et al., 1996). Opsonophagocytic assays have been performed with peripheral blood leukocytes (PBLs) as effector cells and have used a variety of techniques such as radioisotope labeling, flow cytometry, microscopic evaluation and viability assays (Esposito et al., 1990; Guckian et al., 1980; Kaniuk et al., 1992; Lortan et al., 1993; Obaro et al., 1996; Sveum et al., 1986; Vioarsson et al., 1994; Winkelstein et al., 1975). Differentiated HL-60 cells have also been used as an alternative to PBL effector cells, eliminating the need for human donors and decreasing the inter-assay variability that occurs with random PBL donors (Romero-Steiner et al., 1997).

Although functional assays have been developed to measure vaccine efficacy, none of the prior art methods allow the simultaneous detection of functional antibodies generated by multiple serotypes of a pathogen. Detection of functional antibodies to multiple serotypes is essential to the determination of the efficacy of vaccines that include antigens from multiple serotypes. For example, there are multiple serotypes of *Streptococcus pneumoniae*. *S. pneumoniae* is the leading cause of meningitis, septicemia, pneumonia and acute otitis media in young children and an important cause of illness and death in the elderly and persons with certain underlying conditions. Host protection against invasive pneumococcal disease is primarily mediated by anti-capsular antibodies and complement-mediated phagocytosis. Similarly, *Neisseria meningitidis* has several serotypes and protection from disease caused by *Neisseria meningitidis* serogroup A and C is critically dependent upon capsular polysaccharide antibodies. Immunization with meningococcal polysaccharide vaccines elicits complement-dependent serum bactericidal and opsonophagocytic antibodies. Both mechanisms operate simultaneously and function to clear meningococci. However there are individuals incapable of mounting a complement-dependent serum bactericidal response, and for those individuals, opsonophagocytic antibodies serve as the only protection against meningococcal disease. Since functional opsonophagocytic activity appears to correlate with protection against the pneumococcal and meningococcal diseases described above, functional assays will best determine the efficacy of vaccines for these diseases.

Measurement of the effectiveness of a vaccine designed to provide protection against infection by multiple serotypes of *S. pneumoniae* or *N. meningitidis* would require measurement of multiple functional antibodies generated toward each different serotype. Although the functional assays described above could be run multiple times for each different serotype present in the vaccine, such a practice would be arduous and expensive. Therefore, what is needed in the art is a rapid, automated, fictional assay that can simultaneously measure antibodies directed against multiple serotypes of pathogens, particularly those such as *S. pneumoniae* and *N. meningitidis*.

SUMMARY OF THE INVENTION

The present invention relates to methods and compositions directed to measurement of a functional antibody response. These methods and compositions address the continuing need for determination of vaccine protection against pathogens and the ability to test for multiple serotypes.

The present invention comprises methods and compositions for opsonophagocytic assays to measure the presence of functional antibodies. The methods of the present invention comprise the addition of a biological sample to compositions comprising fluorescent beads coated with antigens. Other embodiments of the present invention comprise methods of measuring the presence of functional antibodies comprising addition of a biological sample to compositions of fluorescently labeled bacteria. The compositions of the antibodies of the sample and the fluorescent beads or the labeled bacteria are then added to phagocytic cells for opsonization. A preferred embodiment of the present invention further comprises the addition of complement to complete or enhance the opsonization of the compositions by the phagocytic cells.

Accordingly, it is an object of the present invention to provide methods and compositions for the measurement of the presence of antibodies to a pathogen.

It is another object of the present invention to provide methods and compositions for the detection of the presence of antibodies that provide protection from a pathogen to the human or animal that was the antibody source.

It is yet another object of the present invention to provide methods and compositions that can be used to provide evidence of the efficacy of a vaccine.

It is a further object of the present invention to provide methods and compositions for opsonophagocytic assays.

It is another object of the present invention to provide methods and compositions for opsonophagocytic assays that can be easily determined using flow cytometric methods.

It is an object of the present invention to provide methods and compositions for measurement of functional antibodies using differently labeled fluorescent beads attached to antigens.

It is yet another object of the present invention to provide methods and compositions for measurement of functional antibodies using differently labeled bacteria as the antigen.

These and other objects, features and advantages of the present invention will become apparent after a review of the following detailed description of the disclosed embodiments and the appended claims.

BRIEF DESCRIPTION OF THE FIGURES

FIG. 1 is a chart showing geometric mean titers (GMTs) against *Neisseria meningitidis* in pre- and post-vaccination sera as measured by the serum bactericidal assay (SBA) and the opsonophagocytic assay.

FIG. 2 is a table showing competitive inhibition of opsonophagocytic activity of reference sera after absorption with specific serogroup A and C *Neisseria meningitidis* polysaccharide.

FIG. 3 is a table showing a correlation between SBA, opsonophagocytic assay and ELISA for *Neisseria meningitidis* serogroups A and C.

FIG. 6 is a table showing competitive inhibition of opsonophagocytic activity with type-specific polysaccharide.

FIG. 7 is a table showing a correlation between the flow cytometric and manual viable opsonophagocytic assays.

FIG. 8 is a table showing a comparison of cumulative percentage of serum samples analyzed by two methods.

DETAILED DESCRIPTION

Figure 4:
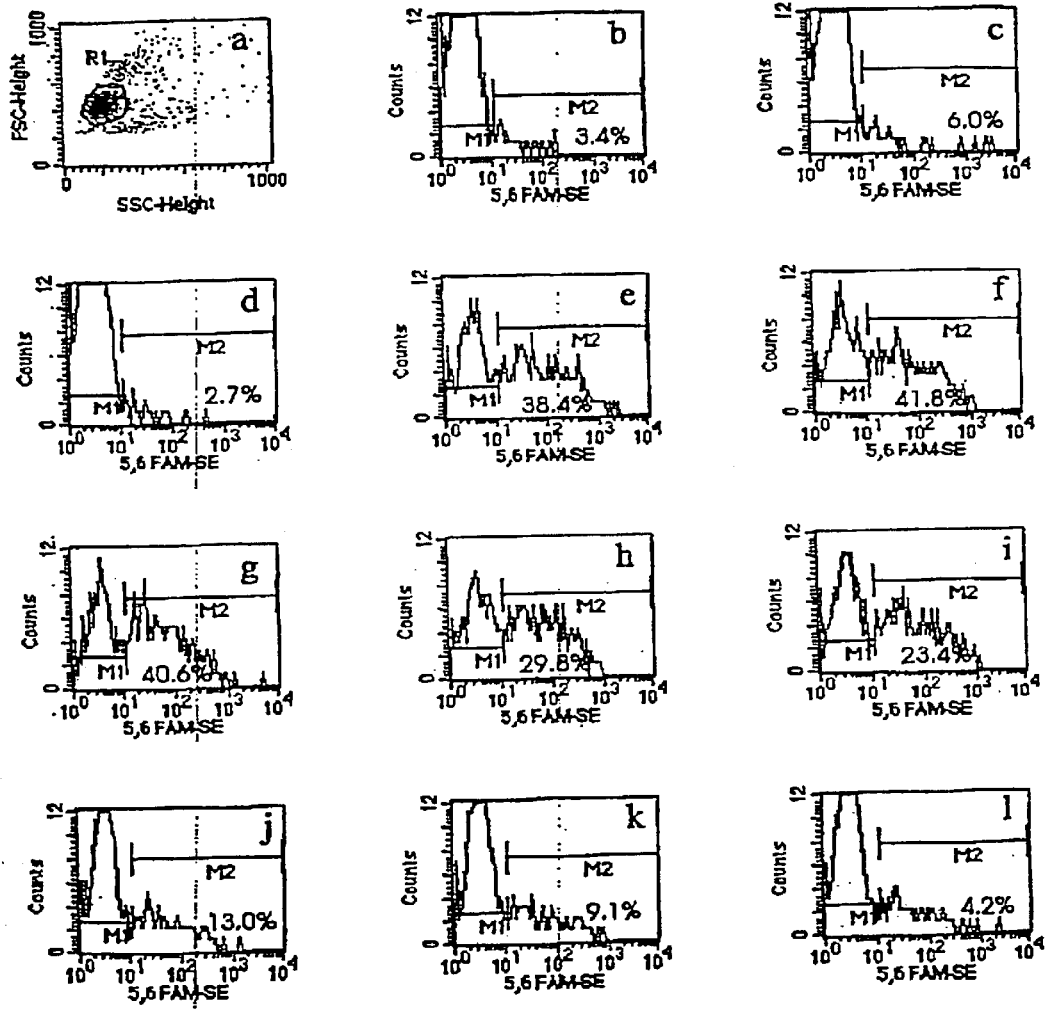
FIGS. 4A–4L are a series of histograms showing flow cytometric analysis of serum with functional antibody.

The present invention comprises methods and compositions that are useful in the measurement of functional antibodies. The present invention comprises methods and compositions for immunoassays that are useful for the simultaneous detection of multiple functional antibodies, each of which are specific for a different antigen in a biological sample. "Functional antibodies" are defined as antibodies that specifically bind to an antigen and also interact with an effector cell, wherein the interaction of the antibody and effector cell results in internalization of the antibody, and any attachments to the antibody, by the effector cell. In a preferred embodiment, the immunoassay is an opsonophagocytic assay, wherein the assay comprises the steps of combining a sample with a plurality of different antigens, complement and effector cells, incubating the combined sample to allow internalization of the antigens by the effector cells, and analyzing the sample. In a preferred embodiment, the sample is analyzed in a flow cytometer, however, it is to be understood that the present invention is not limited to analysis in a flow cytometer and that other means of detection may be used. In a more preferred method, the antigens are labeled bacteria, preferably labeled with fluorescent dyes. In a most preferred embodiment, the antigens are antigens such as peptides, lipids, polysaccharides, nucleic acids or antigenic fragments thereof, that are attached to fluorescent beads. Each differently labeled fluorescent bead has one antigen attached, so that measurement of each of the different fluorescent beads gives a measurement of the different antigens. The presence of functional antibody is indicated by an increase in fluorescence in the effector cells as compared to a control sample. In a most preferred embodiment, the measurement of the fluorescence is made by use of a flow cytometer. It is a surprising finding of the present invention that a plurality of different fluorescent labels can be used simultaneously in a flow cytometer without significant interference among the labels.

In one embodiment of the present invention, the antigens comprise peptides derived from different serotypes or strains of a single pathogenic species. In another embodiment, the antigens comprise peptides derived from multiple pathogenic species. The pathogenic species may be bacterial, viral, fungal or parasitic in nature, but are preferably bacterial. The pathogenic species may be viable or non-viable. Notably, unlike prior art assays that only utilized viable bacteria, the present invention allows the use of non-viable bacteria and thus reduces the health risk to an individual performing the assay. In a most preferred embodiment, the bacterial antigens are derived from *Streptococcus pneumoniae* or *Neisseria meningitidis*. The term "antigen" refers to an entity or fragment thereof which can induce an immune response in a mammal. The term includes, but is not limited to, peptides, lipids, polysaccharides, and nucleic acids containing antigenic determinants recognized by antibodies or other immune cells. The term "antigen" also includes objects such as beads coated with or attached to antigens.

Other important terms as used herein are as follows. The terms "a", "an" and "the" as used herein are defined to mean one or more and include the plural unless the context is inappropriate. The term "antibodies" as used herein includes monoclonal antibodies, polyclonal, chimeric, single chain, bispecific, simianized, and humanized antibodies, including the products of immunoglobulin expression libraries. The phrases "specifically binds to a peptide" or "specifically hybridizes to" or "specifically immunoreactive with", when referring to an antibody, refers to a binding reaction which is determinative of the presence of the peptide in the presence of a heterogeneous population of proteins and other biologics. Thus, under designated immunoassay conditions, the specified antibodies bind preferentially to a particular peptide and do not bind in a significant amount to other proteins present in the sample. Specific binding to a peptide under such conditions requires an antibody that is selected for its specificity for a particular protein. See, Harlow and Lane (1988) *Antibodies, A Laboratory Manual*, Cold Spring Harbor Publications, New York, for a description of immunoassay formats and conditions that can be used to determine specific immunoreactivity.

The effector cells of the present invention are capable of binding to antibody/antigen complexes and internalizing the complexes. Preferably, the effector cells express Fc receptors such as FcRI, FcRII and FcIII that bind to antibody/antigen complexes and facilitate internalization. Examples of effector cells that express Fc receptors are macrophages, mononuclear phagocytes, natural killer cells, and granulocytes such as neutrophils and eosinophils. The effector cells of the present invention may be derived from the serum of an individual or an in vitro culture. In a preferred embodiment, the effector cell is a differentiated human promyelocytic leukemia cell, or HL-60.

In one embodiment of the present invention, the fluorescently labeled antigens comprise intact bacteria that are directly attached to fluorescent molecules. The fluorescent molecules may include, but are not limited to, fluorescein and its derivatives such as 5, 6, carboxyfluorescein succinimidyl ester, ethidium monoazide (EMA), phycoerythrin, allo-phycocyanin, phycocyanin, rhodainine, tetramethylrhodamine, TEXAS RED (sulforhodamine-101-sulfonyl chloride), EDANS (5-((2-aminoethyl)amino) naphthalene-1-sulfonic acid, sodium salt), BODIPY (borondipyrromethene difluoride)dyes, Cy3 and Cy5. The present invention provides methods for an opsonophagocytic assay wherein one or more of fluorescent molecules are used to label, and thereby distinguish, different serotypes of a pathogenic species. The binding of functional antibodies in a biological sample to the differently labeled antigens results in the attachment of a different label to each functional antibody specific for a given serotype antigen. The labels may be differentiated by differences in their emission spectra and/or differences in their fluorescence intensity. For example, in one embodiment of the present invention, functional antibodies specific for four different serotypes of a specific pathogen are simultaneously detected and distinguished, preferably in a flow cytometer, by labeling the antigens bound by those antibodies with different fluorescent colors. Alternatively, the antigens are labeled with the same fluorescent color, but with different fluorescent intensities that are distinguished, preferably in a flow cytometer. As a third alternative embodiment, the four antigens are labeled with two fluorescent colors and the two antigens labeled with the same color are labeled with different fluorescent intensities. As a fourth alternative, the calculated ratio of emission of two or more fluorescent dyes may be used to distinguish individual bacteria or bead populations.

Once the antibody/antigen complex forms in the presence of complement and effector cells, the fluorescent antigen/antibody complexes are internalized by the effector cells. Complement may be provided by the direct addition of complement component C3 or by the addition of other components in the complement cascade that result in the production of C3. One example of suitable complement is described in Example 9. The effector cells are then analyzed, preferably in a flow cytometer, wherein an increase in fluorescence indicates the presence of functional antibody. Functional antibody titers are expressed as the reciprocal of the highest serum dilution yielding $\geq 50\%$ of the maximum phagocytic uptake and samples with a maximum phagocytic uptake of less than 20% are considered negative.

The present invention also comprises measurement of the presence of antibodies using other labels that function as the herein described fluorescent labels or fluorescent beads. It is well within the knowledge of those skilled in the art to use alternative labels, whether fluorescent, radioactive, bioluminescent, chemiluminescent, chemical, enzymatic or others known to those skilled in the art, to provide detection of functional antibodies using the methods and compositions of the present invention. Furthermore, use of alternative labels may call for specific detection apparatus. Additionally, the present invention comprises detection of a label by methods known to those skilled in the art, though the preferred methods of detection comprise the use of a flow cytometer. For example, the present invention comprises, as further described in Example 7, detection of a fluorescent label by using an particle concentration immunofluorescent analyzer, such as the commercially available IDEXX Screen Machine 2000 (Idexx Laboratories, Inc. Westbrook, Me.). Some advantages of using a particle concentration immunofluorescent analyzer platform are that these types of machines are typically easier to use and less expensive than conventional flow cytometry. Further, more serotypes per run can be tested using this platform as opposed to conventional flow cytometry. Additionally, the present invention comprises detection of a fluorescent label by using standard hematology units, such as the commercially available Beckman Coulter Hematology Analyzer described in Example 10.

In an alternate embodiment of the present invention, the fluorescently labeled antigens comprise fluorescent beads attached to or coated with polysaccharide antigens. The fluorescent beads may include, but are not limited to, beads containing fluorescein and its derivatives such as 5, 6, carboxyfluorescein, ethidium monoazide (EMA), phycoerythrin, allo-phycocyanin, phycocyanin, rhodamine, tetramethylrhodamine, TEXAS RED (sulforhodamine-101-sulfonyl chloride), EDANS (5-((2-aminoethyl)amino) naphthalene-1-sulfonic acid, sodium salt), BODIPY (borondipyrromethene difluoride) dyes, Cy3 and Cy5. In a preferred embodiment, the fluorescent beads are coated with antigens by modification of polysaccharide antigens by the addition of an aldehyde group and modification of the beads by the addition of carboxy surface groups as described in more detail below. It is to be understood that the present invention is not limited by the type of bead used, as beads useful for attachment of antigens are known to those skilled in the art, and any structure that is capable of binding antigen and functioning as the described beads herein is encompassed by the present invention. The fluorescent beads may be, but are not limited to, latex beads, polystyrene beads and magnetic beads, however polystyrene beads are preferred. While not wishing to be limited, one example of beads suitable for use in the present invention is described in Example 8.

A most preferred embodiment of the present invention comprises the measurement of functional antibodies to the antigens of *S. pneumoniae* after vaccination of an individual with specific serotype or serotypes of *S. pneumoniae*. The present invention can be used to determine whether the vaccine provides protection for the individual. The antigen composition of *S. pneumoniae* is provided either as killed bacteria or the antigens are attached to labeled beads. A sample from the individual is mixed with the antigen composition, complement is added and the entire mixture is added to phagocytic cells. Uptake of label by the phagocytic cells is measured. Only the presence of functional antibodies, those that can bind the specific antigen and interact with the phagocytic cell and complement, will lead to the uptake of the label by the phagocytic cell.

In another preferred embodiment, the present invention is used to determine the presence of functional antibodies to particular serotypes of *Neisseria meningitidis* after infection or vaccination. The methods are similar to those described above, and the antigen compositions comprise *N. meningitidis* antigens. Again, uptake of label by phagocytic cells is used to determine the presence of functional antibodies.

The present invention is not limited by the specific pathogenic organisms herein described. The present invention contemplates the determination of functional antibodies to any antigen that can be detected by the methods and compositions of the present invention. Any antigen that can function as the antigens herein described, i.e., either by labeling the entire organism or by attaching specific antigenic determinants to beads, for opsonization by effector cells is included in the present invention.

The present invention is useful for the detection of functional antibodies in biological samples such as biological fluids and tissues. The term "biological fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions. The sample may be diluted, purified, concentrated, filtered, dissolved, suspended or otherwise manipulated prior to immunoassay to optimize the immunoassay results.

The present invention is useful for the analysis of vaccine efficacy and the study of immune responses. The effectiveness of a vaccine may be determined using the present invention after administration of the vaccine to an individual. Once the vaccine is administered to the individual and an immune response is generated, a sample suspected of containing functional antibodies may be taken from the individual and analyzed using the methods and compositions of the present invention. The detected amount of functional antibody may then be compared to normal amounts of functional antibody and the effectiveness of the vaccine determined based upon an increase in the amount of functional antibody detected after immunization. The present invention may also be used to study immune responses and determine whether functional antibodies are generated in response to infection by a particular pathogen. For example, the present invention may be used to determine the presence of functional antibodies to provide information regarding an individual's immune response status. For example, if an individual does not mount a particular immune response, due to loss of immune function or a deficit in immune function, the presence of functional antibodies may provide another means of immune protection. The present invention provides rapid and economical means for detecting functional antibodies to determine the immune function of the individual.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of HL-60 Cells

The HL-60 human promyelocytic leukemia cells used as effector cells in the opsonophagocytic assays were prepared as follows. Frozen stocks of the HL-60 cells were quickly thawed and washed two times with room temperature RPMI to remove residual DMSO. The washed cells were then placed into a 75 $cm^2$ tissue culture flask with 20 ml of RPMI+20% FBS and 5 ml 100× pen-strep. The cells were then cultured at 37° C. with 5% $CO_2$. After three days, the culture was examined for growth and viability and 20 ml of fresh RPMI with 20% o fetal calf serum and antibiotics was added. Undifferentiated cells were grown to a density of 4–7×$10^5$ cells/ml with a viability of greater than 90%. Cell densities were kept less than 1×$10^6$ cells/ml. High viability was obtained by feeding (or splitting) the cells roughly on a daily basis.

Differentiation of the HL-60 cells into monocytes was then performed. The HL-60 cells were resuspended in the culture media by gently shaking the tissue culture flask The percentage of cell viability was then determined using trypan blue as follows. Ten microliters of the suspension was added to 10 $\mu$l of 0.4% trypan blue and 10 $\mu$l of opsono buffer into a 1.5 ml eppendorf tube and mixed gently. Ten microliters of the mixture was placed into each chamber of the hemacytometer and a cell count was performed in four outer squares. The number of cells per milliliter was calculated as follows:

a) (N×D)×$10^3$/S×0.1, where N is a number of cells in 4 large outer squares, D is the dilution factor, and S is the number of outer squares counted.

b) Determine the % cell viability as follows:

N/Total number of cells counted×100, where N=total # of cells stained by trypan blue.

Then the volume of un-induced cells (V) required to induce 200 ml of cells at 2×$10^5$ cells/ml was calculated as follows:

2×$10^5$/N×200=V, where N is the number of cells calculated from step (a) above.

A volume of medium equal to 200−V milliliters was added to a tissue culture flask and one mililiter of N-butyric acid/sodium salt (100 mM final concentration) was added to the media in the flask The solution was gently shaken to mix. A volume of cell suspension equal to V was added and the cell suspension was again shaken to mix and incubated for four days at 37° C. in 5% $CO_2$ in a slanted position (5–10°) to give cells larger surface area for differentiation. HL-60 cells were 90–95% differentiated into the monocytic lineage by day four, and were ready to use as phagocytes. Differentiated cells were used at a ratio of 1:1 (target-effector ratio) in the flow opsonophagocytic assay.

EXAMPLE 2

Opsonophagocytic Assay

Human serum to be tested was obtained from immunized individuals and placed in appropriately labeled screw top vials. The serum samples were heat inactivated at 56° C. for 30 minutes. Ten microliters of opsono buffer was added to each well of a 96-well plate except for row A. Also, 10 µl of opsono buffer was added to the complement control wells and 20 µl of buffer was added to cell control wells. Diluted or undiluted test serum (20 µl) was added to the wells of row A. Test serum (rows B–H) was serially diluted (2-fold), resulting in 2-fold dilutions ranging from 1:8 (row A) to 1:1024 (row H). Rows A9–12 were reserved for controls.

Controls consisted of the following:
(1) Positive control (Quality control sera, beads, complement and HL-60 cells)—included in each plate
(2) Complement controls (complement, HL-60 cells and beads without test sera)- included in each row
(3) HL-60 cell control (HL-60 cells and beads only)—included in each row.

The complement control (C') was as follows: Three wells (A12–C12) in each microtiter plate were used for this control. The bead suspension (20 µl) was added to 10 µl of opsono buffer (to replace test sera volume). Complement (10 µl) and HL-60 monocytes (40 µl) were added. The average fluorescence uptake of the three C' wells was measured. Acceptable results were in the range of 1–10%. This control was prepared in the plate and was run at the same time that the samples were run. If the assay consisted of several plates, the average of the C' control wells in each plate was used. This control was run for each serotype assayed. Additionally, quality control sera with known titers was used. Quality control sera with known low, medium, and high titers was included in each assay (wells A10 through A11). The HL-60 cell control was performed to determine the level of phagocytosis as well as clumped beads within the gated cell population that was independent of complement for a given polysaccharide. Twenty microliters of bead suspension was added to 20 µl of opsono buffer (sample and complement volumes replaced) and then HL-60 monocytes (40 µl) were added and incubated 15 minutes at 37° C. with shaking. The amount of phagocytosis was then determined on the flow cytometer to typically be less than 5%.

Once the serum and control samples were placed in the wells, 20 µl of polysaccharide-labeled fluorescent bead suspension was added to each well. The bead suspension consisted of a stock suspension (in Opsono buffer) diluted with opsono buffer to give $1.0 \times 10^5$ beads in 20 µl. This bead suspension was kept in the dark, at room temperature until use. The bead and serum samples were incubated at 37° C. for ninety minutes with shaking. Complement (10 µl) was added to all wells containing sample dilutions, and complement control wells (all wells except the cell control wells). Complement was derived from newborn rabbit serum (Pel-Freez, Brown Deer, Wis.) and was kept frozen at −70° C. in 1 ml aliquots until ready to use. After complement was added, the samples were incubated at 37° C. for 15 minutes with shaking.

HL-60 cells were pre-washed twice in opsono wash buffer (HBSS without $Ca^{++}$ and $Mg^{++}$ with 0.2% bovine serum albumin) and re-suspended in Opsono buffer (HBSS with $Ca^{++}$ and $Mg^{++}$ with 0.2% bovine serum albumin). In the second wash step, the HL-60 cells spent a minimum of 20 minutes in the second opsono wash buffer wash step. Cells were then centrifuged at 1000 rpm for 10 minutes, the supernatant was carefully removed and the cells were re-suspended in opsono buffer to 4 ml (total volume depends upon cell concentration and number of cells needed for the day's run). Total cell count and viability was determined and the cell suspension was diluted to a concentration of $1 \times 10^5$ cells/40 µl. Differentiated HL-60 cells (40 µl) were then added to each well ($1 \times 10^5$ cells/well) and incubated at 37° C. for 30 minutes with horizontal shaking (200 rpm).

Following shaking, 80 µl of sheath fluid was added to each well. In a preferred embodiment, 0.5% paraformaldehyde was added to fix the cells prior to addition of the sheath fluid. The samples were gently mixed with the 200 µl pipettor and transferred to appropriately labeled titer tips. The titer tips were then transferred to appropriately labeled 12×75 plastic test tubes and samples were kept in the dark until analyzed by the flow cytometer.

EXAMPLE 3

Flow Cytometric Analysis

Using CELLQuest software (Becton Dickinson, version 1.2 for Apple System 7.1) on a FACSCalibur Flow Cytometer (Becton Dickinson, San Jose, Calif.) HL-60 cells were readily observable in a forward angle light scatter (FALS) versus side scatter (SSC) dot plot. The instrument settings were as follows:
(a) FALS=voltage E-1, gain 7.50, linear mode
(b) SSC=voltage 300, gain 3.00, linear mode
(c) FL1=530 nm, voltage 600, logarithmic mode.

The analyzed regions were set to include only the viable HL-60 cell population. Non-viable HL-60 granulocytes appeared as a population with intermediate FALS and low to moderate FALS.

The percentage uptake of the beads was determined by calculating the positive and peak channel fluorescence for each sample. The upper limit of the negative (no bead uptake) population was set such that less than 2% of the cell control demonstrated fluorescence above the upper marker channel. The mean peak channel of the negative (without phagocytosis) cell population was dependent upon the FL1 (green fluorescence) detector voltage. The voltage setting was determined empirically. The voltage for FL1 was set such that the negative population was located in the first log decade with the upper limit of the negative population near the transition to the second log decade. The voltage setting was consistent over a period of months and was monitored using standardized fluorescent FITC beads (Becton-Dickinson) to detect any drift due to instrument alterations.

Results were tabulated as the percentage of cells with fluorescence greater than the threshold, wherein the threshold was set as described above. The results indicated the percentage of HL-60 cells with bead uptake. Results were graphed and reported as the reciprocal titer demonstrating greater than or equal to 50% of the maximal uptake for each sera. Thus, the phagocytic titer was observed as a 50% decrease in fluorescence as compared to the highest percent fluorescence of the corresponding control test sample. Serum samples with phagocytic titers less than eight were reported as a titer of four for purposes of data analysis.

EXAMPLE 4

Flow Cytometric Opsonophagocytosis of Latex Beads Coupled with *Neisseria meningitidis* Serogroup A or C Polysaccharide Correlates with Serum Bactericidal Activity To prepare beads coated with polysaccharide from *Neisseria meningitidis*, sodium periodate (MW 213.91) was first dissolved in type I water to a concentration of 10 mg/ml (0.046 M) and wrapped in foil to protect the solution from light. Subsequently, 218 $\mu$l of the stock periodate solution was added to each milliliter of polysaccharide solution (1 mg/ml) prepared by methods known in the art). The reaction progressed in the dark for 30 minutes at pH 7.0 while rotating either at room temperature or 4° C. When the beads were coated with Group A *Neisseria meningitidis* polysaccharide, the reaction was performed at room temperature, and when the beads were coated with Group C *Neisseria meningitidis* polysaccharide, the reaction was performed at 4° C. The reaction was stopped by the addition of 0.1 ml of glycerol per milliliter of reaction solution. The polysaccharide solution was then dialyzed overnight (MWCO 3500) against 0.1 M sodium bicarbonate buffer, pH 8.0.

The above method resulted in a modified polysaccharide containing an aldehyde group. The addition of the aldehyde group was required to facilitate binding of the polysaccharide to the beads; however, modification of the beads was also required. Modification of the beads with addition of carboxy surface groups to provide a reactive terminal hydrazine group was performed as follows. One hundred microliters of the stock solution of beads (FluoSphere beads) were washed twice in 0.1 M sodium phosphate and 0.15 M sodium chloride buffer for 15 minutes at 3,000 rpm. The supernatant was removed and discarded. Adipic acid dihydrazide (32 mg/ml) was dissolved in the sodium phosphate and sodium chloride buffer and 1 ml of adipic acid buffer was added per 100 $\mu$l of bead solution. Water soluble carboiimide EDC (16 mg) was then added and the reaction progressed at room temperature for four hours. Following the reaction, the beads were washed three times and re-suspended in 0.1 M bicarbonate buffer, pH 8.0.

The polysaccharides were then linked covalently to the activated beads as follows. The beads were centrifuged and the supernatant was discarded. One milliliter of the periodate oxidized polysaccharide solution was added to the beads and incubated overnight in the dark at room temperature with rotation. Subsequently, 10 $\mu$l of a 5 M sodium cyanoborohydride solution in 1 N NaOH was added and the reaction allowed to progress for two hours at room temperature. The beads were then washed four times with HBSS$^+$, and finally re-suspended in 1 ml HBSS$^+$ with 0.2% BSA and antibiotics. The beads were stored at 4° C. in the dark.

Thirty-five paired sera using beads coated with either serogroup A or C polysaccharide were tested in the flow cytometric opsonophagocytic assay as described above and also the standardized serum bactericidal assays (SBAs). As shown in FIG. 1, the two functional assays yielded similar geometric mean titers (GMTs) of functional antibodies. SBA geometric mean titers for pre- and post-vaccination sera were 612 and 10,023 for serogroup A, and 46 and 2,649 for serogroup C, respectively. Flow opsonophagocytic GMTs for pre- and post-vaccination sera were 412 and 16,712 for serogroup A and 86 and 4,993 for serogroup C, respectively.

The specificity of the opsonophagocytic assay was determined by competitive inhibition of the opsonophagocytic activity of reference sera with specific serogroup A and C *Neisseria meningitidis* polysaccharide (200 $\mu$g/ml). Absorption of these sera with serogroup specific polysaccharide resulted in a 99.2% mean decrease for serogroup A and a 98.4% mean decrease for serogroup C. These data are summarized in FIG. 2.

Correlations between the SBA, the flow cytometric opsonophagocytic assay and a standardized enzyme linked immunosorbant assay (ELISA) were also examined. The results are listed in FIG. 3. All three assays demonstrated significant correlation to each of the other assays. Although the SBA and opsonophagocytic assays are different functional assays, the calculated titers did not differ significantly for serogroup A ($P=0.44$) or for serogroup C ($P=0.19$) by paired t-test. The opsonophagocytic assay also showed good precision with 96% and 83% of titers within three dilutions of the median SBA titer for serogroups A and C respectively.

EXAMPLE 6

Correlation between Multicolor Flow Cytometric Opsonophagocytic Assay and Manual Viable Bacterial Cell Assay All serum samples (28 pre-vaccination and 36 post-vaccination serum samples) were collected after informed consent was obtained from healthy adult volunteers. Sixteen serum samples were collected through the Emory University Donor Services (Atlanta, Ga.) and 234 paired serum samples previously used in a multi-laboratory ELISA validation study (18) were collected through the National Blood Service (Oxford Centre, Oxford, England). Post-vaccination serum was collected four to six weeks after immunization with the 23-valent pneumococcal polysaccharide vaccine (Lederle Laboratories, Praxis-American Cyanamid Co., J. Pearl River, N.Y.). All serum samples were stored at -70° C. and were heated to 56° C. for 30 minutes just prior to testing to inactivate endogenous complement activity.

All strains of *S. pneumoniae* were recent clinical isolates used in the standardized viable opsonophagocytic assay and were stored at 76° C. Briefly, the bacteria were incubated overnight on blood agar plates (Life Technologies, Grand Island, N.Y.) at 37° C. in 5% $CO_2$. The isolated colonies were then inoculated into Todd-Hewitt broth with 0.5% yeast extract and were incubated without shaking for three to four hours at 37° C. in 5% $CO_2$. Bacteria were harvested by centrifugation at 800×g for 10 minutes at room temperature and were suspended in 5 ml of bicarbonate buffer (0.1 M $NaHCO_3$, pH. 8.0). Fifty microliters of 5,6 carboxyfluorescein, succinimidyl ester FAM-SE (Molecular Probes, Eugene, Oreg.) solution (10 mg/ml in dimethyl sulfoxide (Fisher Scientific Co. Fair Lawn, N.J.)) was added, and the mixture was incubated for one hour without shaking at 37° C. in 5% $CO_2$. Finally, 1 ml of 2% paraformaldehyde (Sigma Chemical Co., St. Louis, Mo.) was added, and fixation was allowed to proceed overnight at 37° C. without shaking. To confirm that the labeled bacteria were nonviable, 0.1 ml of bacterial suspension was cultured on a blood agar plate and the plate was incubated overnight as before. The labeled bacteria were washed by centrifugation six times in 20 ml of opsonophagocytosis buffer (Hanks balanced salt solution with $Ca^2$ and $Mg^2$ (Life Technologies), 0.2% bovine serum albumin (Sigma), and 1× penicillin-streptomycin (Life Technologies)) until no free dye was observed in the supernatant FAM-SE labeled bacterial were counted with the BacCount kit (Molecular Probes). FAM-SE labeled bacteria were stored at 4° C. under protection from light and were stable for a minimum of three months. Bacterial concentrations were adjusted to a concentration of $4 \times 10^5$ bacteria in 40 µl prior to use. The presence of a capsule was verified by the Quelling reaction before and, after FAM-SE labeling, and no significant differences were observed.

HL-60 (human promyelocytic leukemia cells: CCL240, American Type Culture Collection, Rockville, Md.) were grown to a cell density of $4 \times 10^5$ to $6 \times 10^5$ cells/ml in 80% RPMI 1640 medium that contained 1% 1-glutamine but no phenol red (Life Technologies) and that was supplemented with 20% heat-inactivated fetal bovine serum (HyClone Laboratories, Logan, Utah) and 1× penicillin-streptomycin. These cells were differentiated into granulocytes by culturing in the same medium supplemented with 100 mM N,N dimethylformamide (99.8% purity; Fisher Scientific) for a period of 5 days. The flow cytometric opsonophagocytosis assay required differentiated HL-60 granulocytes with high degrees of viability ($\geq 90\%$, as judged by 0.4% trypan blue exclusion staining). Such a high degree of cell viability was obtained by daily feeding or division of the undifferentiated HL-60 cell line stock Adequate phagocytosis was observed in differentiated HL-60 cells through at least 230 passages.

Differentiated HL-60 cells were harvested by centrifugation at 160×g for ten minutes and were washed twice in 15 ml of wash buffer containing Hanks balanced salt solution without $Ca^{++}$ and $Mg^{++}$, 0.2% bovine serum albumin and 1× penicillin-streptomycin. The cells were then washed once in opsonophagocytosis buffer and were re-suspended in 4 ml of opsonophagocytosis buffer and counted in a hemacytometer. The cell concentration was adjusted to $1 \times 10^5$ cells per 80 µl volume resulting in an effector cell/target cell ratio of 1:4.

Eight twofold serum dilutions were made in opsonophagocytosis buffer from 20 µl of test serum. A 40 µl aliquot of bacterial suspension containing $4 \times 10^5$ bacteria was added to each well and the plate was incubated for 30 minutes at 37°C. in room air with horizontal shaking (200 rpm). Then 20 µl of 3- to 4-week-old, sterile baby rabbit serum (Pel-Frez Brown Deer, Wis.) was added to each well with the exception of the HL-60 cell control wells, which received 20 µl of opsonophagocytosis buffer. After incubation at 37° C. in room air for 15 minutes with shaking, 80 µl of washed differentiated HL-60 cells ($1 \times 10^5$ cells) was added to each well and the plates were incubated with shaking at 37° C. in air for 15 minutes. The final well volume was 160 µl. An additional 80 µl of opsonophagocytosis buffer was added to each well to provide sufficient volume for flow cytometric analysis, and the well contents were re-suspended and transferred to titer tubes (Bio-Rad Laboratories, Richmond, Calif.). The titer tubes were placed inside 12×75-mm polystyrene disposable tubes for flow cytometric analysis. The samples were stored in the dark and on ice until they were analyzed. Samples were typically analyzed within three to four hours without affecting the results and were held for as long as six hours without affecting the observed titer. The tubes were vortexed for three seconds before sampling in the flow cytometer.

Three controls were included per assay for each serotype assayed, (1) HL-60 cell control containing only cells and bacteria, (2) three complement controls containing all test reagents except antibody source, and (3) a positive quality control serum sample, which was a post-vaccination serum sample with a known opsonophagocytic titer. The positive quality control serum sample was included on every microtiter plate. Manual opsonophagocytic assays were performed as described previously (Romero-Steiner et al., 1997). Using the manual assay, no difference between human and baby rabbit serum as a complement source was observed, however only the rabbit complement was used for the development and standardization of the flow cytometric assay.

Samples were assayed with a FACSCalibur immunocytometry system (Becton Dickinson and Co. Paramus, N.J.) and were analyzed with CELLQuest software (version 1.2 for Apple system 7.1, Becton Dickinson). A minimum of 3,000 gated HL-60 granulocytes were analyzed per tube. FAM-SE was excited at a wavelength of 488 nm, and the FAM-SE fluorescence signals of gated viable HL-60 cells were measured at 530 nm. The upper limit of the background fluorescence was measured in the HL-60 cell controls and consisted of auto-fluorescence of HL-60 cells, nonspecific adherence of bacteria, and bacterial clumps. A marker region (M1) was superimposed above, the cell control fluorescence peak to include 98% of the population. A second marker region (M2) was used to determine the percentage of differentiated HL-60 cells with fluorescence greater than that of M1 for each serum dilution. The cells in this region had phagocytosed *S. pneumoniae*. Titers were reported as the reciprocal of the highest serum diffusion yielding $\geq 50\%$ of the maximum phagocytic uptake. Samples with a maximum phagocytic uptake <30% were considered negative and were reported to have a titer of four.

A panel of pre-vaccination serum samples (n=5), post-vaccination serum samples (n=5), and Sandoglobulin, a pooled immunoglobulin G (IgG) antibody preparation (Sandoz Pharmaceuticals Co., East Hanover, N.J.) at a concentration of 6% was tested for opsonophagocytic antibodies to seven pneumococcal serotypes (serotypes 4, 6B, 9V, 14, 18C, 19F, and 23F) after pre-absorption for 30 minutes at room temperature with equal volumes of either homologous or heterologous polysaccharide (American Type Culture Collection) diluted to a final concentration of 0.5 mg/ml. Competitive inhibition with homologous polysaccharide was performed only with the post-vaccination sera. The samples were competitively inhibited and were tested in triplicate. The results were analyzed by the Wilcoxon rank sum test for statistical differences as described below.

Pearson's product moment correlation coefficient for normally distributed data was determined and Wilcoxon rank sum tests for non-parametric data were performed with the SigmaStat software program version 2.0 (Jandel Scientific, San Rafael, Calif.). Significant levels were set at P values of <0.05. Differences between paired data were determined by paired t test. The geometric 95% confidence interval (GCI) was estimated as the geometric mean titer (GMT)± (geometric standard error×1.96).

In the flow cytometric opsonophagocytosis assay, FAM-SE-labeled pneumococci were opsonized by type-specific anti-capsular antibodies in an antibody concentration and complement-dependent manner. Functional antibody activity against seven pneumococcal serotypes (serotypes 4, 6B, 9V, 14, 18C 19F, and 23F) was measured in pre- and post-vaccination serum samples and functional antibody activity was demonstrated by increased fluorescence of HL-60 PMNs containing phagocytosed FAM-SE labeled pneumococci (FIG. 4). The opsonophagocytosis, i.e., fluorescence, was dependent upon the amount of functional antibody present in each sample and behaved in an antibody concentration-dependent manner, as illustrated in FIG. 4.

The percentage of HL-60 PMNs containing phagocytosed pneumococci decreased as the amount of functional antibody was decreased by dilution. The percentage of HL-60 PMNs containing fluorescent pneumococci was then plotted for each sample's dilution series to determine an opsonophagocytic titer for each sample.

In particular, FIG. 4 shows a flow cytometric analysis of serum with functional antibody activity by differentiated HL-60 granulocytes. Panel a shows a scattergram of the forward light scatter versus the side light scatter. Gated cells (dark gray) represent the viable singlet population of differentiated HL-60 cells. Panel b is a histogram representation of the gated HL-60 cells with varying degrees of fluorescence caused by uptake of 5,6 FAM-SE labeled pneumococci in the HL-60 control. M1 was adjusted to encompass 98% of the gated HL-60 cells and M2 defines the fluorescent gated HL-60 population. The percentage of cells in M2 are shown. Panel c is a histogram representation of uptake in the complement control. Panel d is a histogram representation of a pre-vaccination serum diluted 1:8 (serotype 6B). Similar profiles were obtained at higher dilutions of the pre-vaccination serum shown. Panels e, f, g, h, I, j, k and L are the fluorescence profiles of the HL-60 granulocytes (n=3,000) in the presence of post-vaccination serum diluted at $\frac{1}{8}$, $\frac{1}{16}$, $\frac{1}{32}$, $\frac{1}{64}$, $\frac{1}{128}$, $\frac{1}{256}$, $\frac{1}{512}$, and $\frac{1}{1024}$, respectively.

Figure 5:
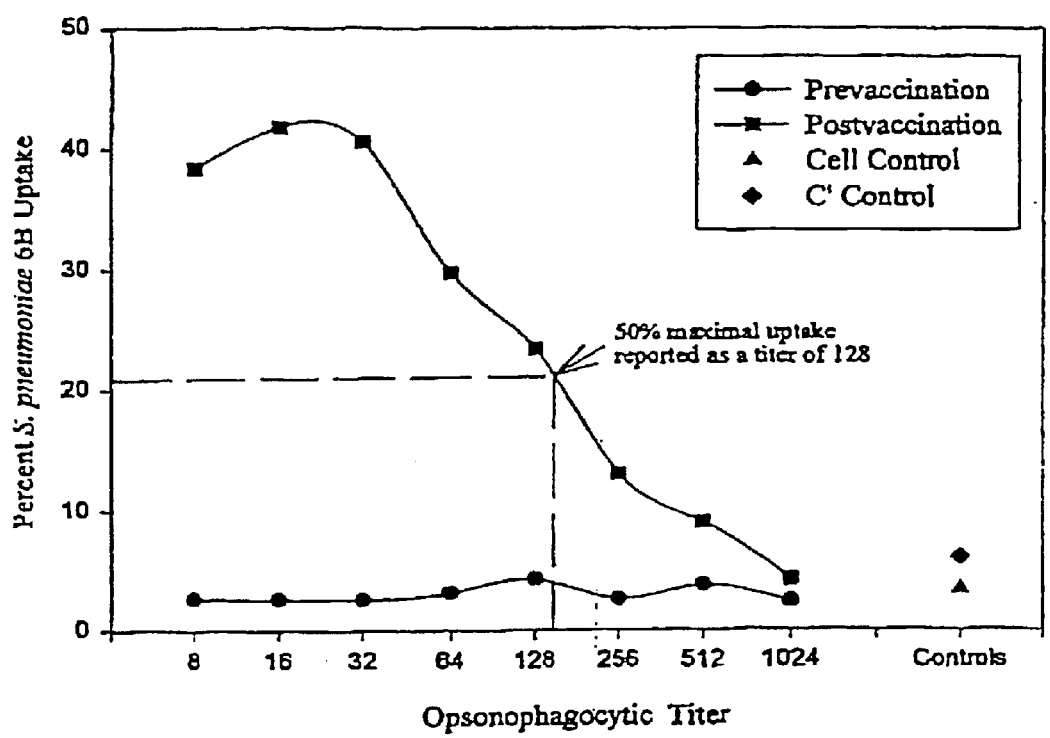
FIG. 5 is a graph showing a dilution curve of the functional opsonophagocytic activity in post-vaccination serum.

FIG. 5 shows the differences in the percent uptake between a pre- and a post-vaccination serum sample. FIG. 5 also shows the opsonophagocytic titer for the post-vaccination serum sample. The opsonophagocytic titer was the reciprocal of the dilution with >50% maximum uptake observed in each serum, in this case, a titer of 128 (arrow). A dilution curve of the opsonophagocytic activity in the corresponding pre-vaccination serum (panel d in FIG. 4) is shown for comparison. The titer for this non-immune serum was <8. Competitive inhibitions with homologous polysaccharide and with a panel of quality control serum samples resulted in $\geq 97\%$ inhibition for all seven serotypes tested (FIG. 6).

The maximum percent uptake of FAM-SE labeled pneumococci by differentiated HL-60 cells in post-vaccination serum was similar for all serotypes tested, with a mean±1 standard deviation uptake for all serotypes of 40%±10.6%. The maximum percent uptake was serum dependent. The range of percent uptake observed in the complement controls was also similar for each serotype tested, with a mean of 9%±1.2%. Similar percent uptakes were observed for PMNs isolated from different donors. For example, in a representative experiment, maximum uptakes (reported titer) for serotype 14 were 49.6% (256) and 48.7% (512) for PMNs isolated from whole blood and HL-60 PMNs, respectively. Measurement of ingested bacteria as opposed to adherent bacteria was confirmed by trypan blue quenching of the fluorescent FAM-SE signal. No appreciable reduction in the signal was observed in the fluorescent FAM-SE signal with the addition of 0.4% trypan blue. We examined different HL-60 bacteria ratios, from 4:1 to 1:100 HL-60 cells/bacteria. HL-60/bacteria ratios between 1.2 and 1:10 resulted in maximal percent phagocytosis in post-vaccination serum, with minima increases ($\leq 10\%$ uptake) in phagocytosis in the complement-containing control (data not shown).

The serotype specificity of the flow cytometric opsonophagocytic assay for type 4, 6B, 9V, 14, 18C, 19F, or 23F was evaluated in five post-vaccination serum samples by pre-incubation with heterologous polysaccharide in a checkerboard design. Of 42 combinations of heterologous pre-absorption, only 1 produced a significant reduction in mean titer compared to that for the unabsorbed serum sample. Pre-adsorption of serum with a type 9V polysaccharide produced a mean titer inhibition of 17.4% in the serotype 4 assay (P<0.001).

By contrast, when a pooled antibody preparation, Sandoglobulin, was cross absorbed with heterologous polysaccharide, a significant reduction in flow cytometric opsonophagocytic titers was observed by the Wilcoxon rank sum test for antibodies against serotypes 4 (24% decrease, P=0.02), 9V (58% decrease, P=0.03), and 14 (22% decrease, P=0.02). The reductions in heterologous polysaccharide-absorbed Sandoglobulin titers were not significant for serotypes 6B (22% decrease, P=0.08), 18C (38% decrease, P=0.06), and 23F (25% decrease, P=0.06).

The reproducibility of the flow opsonophagocytic assay was assessed in 68 replicates (all serotypes included) of a single quality control serum; 65% gave the median titer, the titers for 87% of the assays were within±1 dilution of the median titer, and the titers for 97% of the assays were within±2 dilutions of the median titer. The geometric 95% confidence intervals (G95% Cis) for a panel of quality control serum samples (n=4) were determined by testing each serum sample three to six times against each serotype. The GMTs and G95% Cis for each serotype were as follows: serotype 4, 675 and 406 to 1,063; serotype 6B, 260 and 169 to 388; serotype 9V, 2,474 and 1,783 to 3,326; serotype 14, 664 and 388 to 1,176; serotype 18C, 546 and 338 to 891; serotype 19F, 276 and 194 to 388; and serotype 23F, 659 and 416 to 1,024. These G95% Cis represent less than one dilution from the GMT for all serotypes tested.

Overall, the results of the flow cytometric assay correlated well (r=0.89 and P$\leq$0.001) with those of the manual viable assay for all seven serotypes tested. The correlations per serotype are given in FIG. 7. The GMTs obtained by the flow cytometric assay with post-vaccination serum samples were higher in for serotypes 9V, 14 and 18C and lower for serotype 4 than those obtained by the manual viable assay. These differences were not significant for serotype 4 (P=0.117), serotype 14 (P=0.05), or serotype 18C (P=0.114) by paired t test A significant difference was only found for serotype 9V (P<0.001). Pre-vaccination GMTs were very similar by both methods. Additionally, in a subsequent experiment, r values of 0.96 0.90 and 0.81 were obtained for serotypes 1, 6B and 9V of S. pneumoniae, respectively.

Fifty-two percent of the serum samples tested against all serotypes by the flow cytometric assay gave the same titer as the manual viable assay, 73% gave titers within±1 dilution of those of the manual viable assay. Eighty five percent gave titers within±2 dilutions of those of the manual viable assay, and 93% gave titers within±3 dilutions of those of the manual viable assay. In general, the flow cytometric assay tended to give the same opsonophagocytic titers or titers one dilution higher than those achieved by the manual viable assay (FIG. 8). For all serotypes, the flow cytometric opsonophagocytic assay values were normally distributed around the median value for the manual opsonophagocytic assay. The flow cytometric assay allowed a higher number of serum samples to be analyzed daily, approximately 50 serum samples per eight hours, as opposed to the approximately 25 serum samples that could be analyzed in 18 to 24 hours by the manual viable opsonophagocytic assay. The flow cytometric assay was unaffected by the presence of penicillin (0, 100, or 1,000 units/ml) in the assay buffers since no significant differences in opsonophagocytic titer were observed in a panel of six serum samples tested for antibodies or serotypes 6B (P=0.49) and 18C (P=0.57).

EXAMPLE 7

Detection of Intracellular Fluorescence Using Latex Particle Concentration Fluorescence Immunoassay on an IDEXX Screen Machine 2000

The process of detecting intracellular fluorescence using latex particle concentration fluorescence immunoassay on a particle concentration immunofluorescent analyzer, such as the IDEXX Screen Machine 2000 (Idexx Laboratories, Inc. Westbrook Me.) is described below.

Particle Concentration Fluorescence Immunoassays are adapted to Opsonic Functional Antibody Detection by the use of sub micron latex particles. Particles coated with bacterial antigen as the solid phase are used for performing whole cell fluorescent multiplexed antigen detection. Current conjugate and combination vaccine new drug investigations make it desirable to achieve detection of seven, nine and eleven serotype specific opsonic antibodies in a single assay. Particle Concentration fluorescent immunoassays make this possible.

Particles are prepared with varying fluorescent dyes and dye concentrations to produce a matrix of identically sized particles that vary in staining characteristics by virtue of dye color or intensity of stain. These differing characteristics produce unique populations of stained particles. Each population is differentially coated with a single investigational antigen or single antigenic serotype. Coating is achieved by methods of a proprietary solid phase amino-polysaccharide coupling process. Coated particles are mixed to prepare an investigational matrix solution containing up to 12 antigens or serotypes. Each serotype and the attendant mix of serotypes are custom blended specific for the investigational vaccine.

Mixed particles are added to and reacted with serum test samples from immunized individuals of the study population. The reaction is performed in 96 well fluoricon glass fiber membrane vacuum filtration assay plates. Following an incubation period, lyopholized 3–4 week baby rabbit serum is added as a source of comnpliment. The mixture is incubated. Following incubation, differentiated HL-60 cells (or suitable replacement) are added as effector cells to complete the opsonic-phagocytic reaction.

When the reaction is complete, separation of engulfed particle from free particles is achieved by vacuum filtration. The cells are then washed and total intracellular fluorescence is measured on the IDEXX Screen Machine 2000. The method of detection is front surface fluorimetry using a photo multiplier tube through fluorophore-specific interference filter packs. Detection of a particular fluorescent dye or differential dye concentration is evidence of an engulfed antigen-bead-antibody opsonin and indicates the presence of opsonic antibodies expressing specificity for a particular investigational antigen.

Detection on the Screen Machine 2000 is achieved by the use of four fluorescent channels, each with specific combinations of excitation and emission bandpass filters and a long pass diachronic mirror. Fluorescent channels are completely user selectable and each channel is individually referenced. Eight individual channel gain selections are programmable for each fluorescent channel, allowing protocol-optimizing configurations. Any combination of these four channels may be used for a given plate read. Multiplexed antigen detection exceeding 12 populations is therefore achievable.

Data reduction can be accomplished with IDEXX Windows based WinPlate data collection and analysis software or other custom created software for the IDEXX Screen Machine.

EXAMPLE 8

Bead Specifications for Multicolor Multiplexed Opsonophagocytic Detection of Pathogenic Antigens Including *S. pneumoniae*

The intact bacterium multicolor opsonophagositic assay method described above can be replaced, creating benefits including much greater "standarization" and greater "automation" on the flow cytometer, IDEXX machine and standard hematology units by using latex beads coated with antigens specific to the targeted serotype as a replacement to the intact bacterium. The beads are described as follows:

1. Bead size nominal 1 micron for flow cytometric assays.
2. Bead size nominal 0.8 microns or smaller for Particle Concentration Fluorescence Immunoassay (PCFIA).
3. Bead size to vary between 0.5 microns and 8 microns for Volume/conductivity/Laser Light scatter (Coulter VCS) Technology applications
4. All bead populations must be same size (CVs 20% or less), minimal aggregation of beads in final product.
5. For Flow Cytometry: Bead populations must be discriminated on the basis of dye concentrations (determined by running on cytometer) for three different dyes:
   a) Dyes must be detectable utilizing BD standard filter set-up for three color Caliburs, note the dyes should be chosen to minimize crosstalk between detectors.
      1. Must be excited at 488 nm
      2. Dye 1 detected on FL1 at 525 nm
      3. Dye 2 detected on FL2 at 575 nm
      4. Dye 3 detected FL3 at >600 nm
   b) Individual dye concentrations in a bead population must increase in such concentrations that will yield 1 log decade increases in peak channel fluorescence for that bead population compared to the previous bead population as detected on a flow cytometer.

For Flow Cytometry: The bead populations are visualized s a matrix on a dot plot of FL1 v FL2, or FL1 v FL3, or FL2 v FL3
   a) This yields total number of possible bead populations of $4^3$ or 64 different bead populations when all three dyes are considered.
   b) Mean channel fluorescence must have small CVs (2%)
1. Bead populations will have appropriate amino functional groups on surface to optimize bacterial capsular polysaccharide attachment.
2. Attach *S. pneumoniae* and *Nisseria mennigitidis* polysaccharide, or other identifiable compound specific to the targeted serotype, according to the following protocol:
   a) Prepare a solution of 1 mg. sodium m-periodate in 1 ml of distilled-deionized water.
   b) Add dropwise with stirring the solution from step a) to a solution containing 10 mg. of bacterial capsular polysaccharide in 2 ml. of distilled-deionized water.
   c) Stir mixture for 30 minutes at room temperature.
   d) Add 10 micro liters of 1 molar ethylene glycol to the mixture
   e) Stir for five minutes
   f) Pack 5 ml of a 5% w/v suspension of amino polystyrene particles by centrifugation at 4000×g for ten minutes. Decant.
   g) Add mixture from steps a through e to the packed beads.
   h) Adjust pH of the mixture to a range of 9.0 to 9.5 with 10% K2CO3 i) Stir mixture at room temperature for 1 hour.
j) Add 6 mg of sodium cyanoborohydride to the mixture.
k) Stir for 12 hours.
l) Wash particles twice with distilled-deionized water.
m) Resuspend particles in 5 ml of 0.1 molar PBS containing 100 mg bovine serum albumin (BSA).
n) Stir mixture at room temperature for two hours.
o) Wash particles twice with distilled-deionized water
p) Resuspend particles in 5 ml of 0.1 molar PBS to give 5 ml's of 5% s/v suspension.
3) Shelf life of beads with attached polysaccharide is to exceed six months.

EXAMPLE 9

Freeze Drying Baby Rabbit Serum for use as a Complement Source in Opsonophagocytic Multiplexed Antigen Detection Assays One embodiment of the opsonophgocitic assay process requires the use of complement to mimic the "in vivo" climate. Typically baby rabbit serum complement is used as it is commercially available and has proven to be compatible with the processes described above. Other complement can be used and the following "Freeze drying process" can also be adapted to it.

Use of complement, in its presently available form, in the opsonphagositic assay process, especially for the contemplated wide spread commercial application of the multi-color opsonphagositic assay processes described above is suitable for use with the present invention. However, conventional complement may create a number of problems in the commercial lab setting.

The problems include, but are not limited to the following:

1. Tests have to be accurately anticipated and viable complement has to be ordered, obtained and readied shortly before the test is run, using valuable man hours.
2. The viability or shelf life of complement, in its presently used form for this process, is less than optimum for the "commercial setting" "lowtech" label.

The problems described above, and others, can be solved by "freeze drying" or "lyophilizing" the complement as described below, creating long shelf life and allowing the customer, lab, lab tech or "tester" to keep expensive usable complement on hand for use when needed with a minimum of man hours and set up time. This type of complement in is suitable for use in "commercial kits" utilizing the above described multi-color opsonphagcytic technology.

Process Description:

1. Obtain 3–4 week baby rabbit serum, or other suitable complement.
1. Thaw frozen baby rabbit serum in cold water, approximately 1 hour
2. While serum is thawing prepare labeled sterile glass vials (3 ml size).
4. After serum is thawed, gently mix to ensure complete thawing and mixing of serum. Note: a small amount of ice is acceptable.
5. Under sterile conditions aliquot 1 ml of serum into labeled vials, and cap with sterile rubber stoppers. Note: The stoppers are not completely pushed into vials, allow sufficient space to allow vacuum to equalize and for sublimated water to escape during processing.
6. Snap freeze aliquoted serum in a dry ice/alcohol bath.
7. Immediately after freezing transfer tray of frozen aliquots to interior of lyophilizer (pre-cooled). At no time should the serum be heated or allowed to thaw again.
8. Initiate freeze drying cycle. Note: At the end of the freeze dry cycle, the temperature of dried aliquots should be allowed to rise slowly to room temperature (no additional heating during cycling). The entire process takes approximately 24–48 hours.
9. Upon completion of drying cycle, the rubber stoppers are pressed in completely and aluminum covers crimped on.
10. Freeze dried serum is stored at 2–4° C. until used.
11. Freeze dried serum is reconstituted 5–10 minutes prior to use by the addition of 1 ml sterile DI water.

EXAMPLE 10

Antigen Coated Opsonophagocytic Latex Particle Volume Conductivity and Laser Light Scatter Detection on Beckman Coulter Hematology Analyzers Current new drug investigations work on conjugate and combination vaccine makes it possible to produce custom vaccines or custom administration of single valent vaccines. These vaccines can be effective against multiple pathogens. Idiotypical, serotype specific, susceptibility, may be problematic in specific sub-population of individuals. Examples of sub-populations are patients with AIDS, splenectomized and immunocompromised individuals. For the purpose of disease management and vaccine therapy, it is therefore desirable to achieve species or serotype specific functional opsonic antibody detection from fluid or tissue sample of individuals. Qualitative opsonic antibody detection is possible in a clinical setting utilizing widely available common blood cell analysis technology.

Phagocytized Differential Particle Detection in Opsonic Immunoassays are adapted to Beckman Coulter Hematology analyzer series: GEN-S, STKS, MAXM, and HEMAX. These analyzers utilize Coulter VCS Technology.

Evidence of the presence of opsonic functional antibodies is achieved by the use of a panel of antigen coated submicron latex particles of various sizes and densities. Particles coated with bacterial antigens serve as the solid phase for performing whole cell multiplexed, discrete or simultaneous multiplexed antigen detection.

Particles are prepared in a variety of sizes and densities from materials such as polystyrene or others. Additionally, particles are prepared with varying surface functional group molecular attachment expressions. A panel of differential surface altering R group attachments is therefore possible. Specific R group coupling of surface molecules is achieved to give each population of particles different physical characteristics properties for the measurement parameters of: (1) particle volume, (2) radio frequency conductivity and (3) laser light scatter. These differing characteristics produce unique populations of particles. Each population is differentially coated with a single investigational antigen or single antigenic serotype. Coating may be achieved using a Flow Applications Inc. (Okawville, Ill.) solid phase functional group-antigen coupling process. Coated particles are used as single or mixed serotype solutions.

Single serotype particle solutions are added to and reacted with serum test sample from treatment individuals. The reaction is performed in a standard 96-well micro-titer plate or other suitable vessel. Each serial dilution row is a single serotype test. Following an incubation period, lyopholized 3–4 week baby rabbit serum is added as a source of complement. The mixture is incubated. After incubation, differentiated HL-60 and or other cells are added, in excess, in a matrix model, as effector cells. Opsonophagocytosis of the particle is accomplished during incubation. Cells are washed by common methods and resuspended for analysis.

When the reaction is complete, the solutions are assayed one at a time or as a multiplexed mixture on the "Differential Channel" of the VCS analyzer. A discrete cell or particle population with measurements for volume conductivity and scatter, whether intracellular or liberated by cellular lysis, is evidence of an engulfed antigen-bead-antibody opsonin. Evidence of such a cell, population of cells, or the inclusion remnants there-of, proves the presence of opsonic antibodies expressing specificity and avidity for the particular investigational antigen.

Modifications and variations of the present method will be obvious to those skilled in the art from the foregoing detailed description. Such modifications and variations are intended to come within the scope of the appended claims.

REFERENCES

Each of the below listed references are incorporated by reference.

DeVelasco, A. E., A. F. M Verheul, A. M. P. Van Steijn, H. A. T. Dekker, R. G. Feldman I. M. Fernandez, J. P. Karmerling, J. F. G. Vliegenthart, J. Verhoef, and H. Snippe (1994) Epitope specificity of rabbit immunoglobulin G (IgG) elicited by pneumococcal type 23F synthetic oligosaccharide and native polysaccharide-protein conjugate vaccines: comparison with human anti-polysaccharide 23F IgG. Infect. Immun. 62:799–808.

Esposito, A. L., C. A. Clark, and W. J. Poirier (1990). An assessment of the factors contributing to the killing of type 3 *Streptococcus pneumoniae* by human polymorphonuclear leukocytes in vitro. APMIS 98:111–21.

Guckian, J. C., G. D. Christensen, and D. P. Fine (1980). Role of opsonin in recovery from experimental pneumococcal pneumonia J. Infect. Dis. 142:175–90.

Kanuik, A. St. C., J. E. Lortan, and M. A. Monteil (1992). Specific IgG subclass antibody levels and phagocytosis of serotype 14 pneumococcus following immunization. Scand. J. Immunol. 36 (Suppl. 11):96–98.

Lortan, J. E., A. St. C. Kanuik, and M. A. Monteil (1993). Relationship of in vitro phagocytosis of serotype 14 *Streptococcus pneumoniae* to specific class and IgG subclass antibody levels in healthy adults. Clin. Exp. Immunol. 91:54–57.

Nahm, M. H., G. R. Siber, and J. V. Olander (1996). A modified Farr assay is more specific than ELISA for measuring antibodies to *Streptococcus pneumoniae* capsular polysaccharides. J. Infect. Dis. 173:113–18.

Obaro, S. K., D. C. Henderson, and M. A. Monteil (1996). Defective antibody-mediated opsonization of *S. pneumoniae* high risk patients detected by flow cytometry. Immunol. Lett. 49:83–89.

Quataert, S. A., C. S. Kirch, L. J. Quackenbush Wiedl, D. C. Phipps, S, Stromhmeyer, C. O. Cimino, J. Skuse, and D. V. Madore (1995). Assignment of weight-based antibody units to a human antipneumococcal standard reference serum lot 89-S. Clin. Diagn. Lab. Immunol. 2:590–97.

Romero-Steiner, S., D. Libutti, L. B. Pais, J. Dykes, P. Anderson, J. C. Whitin, H. L. Keyserling, and G. Carlone. (1997). Standardization of an opsonophagocytic assay for the measurement of functional antibody activity against *Streptococcus pneumoniae* using differentiated HL-60 cells. Clin. and Diag. Lab. Immunol. 4:415–22.

Schiffman, G., R. M. Douglas, M. J. Bonner, M. Robins, and R. Austrian (1980). A radioimmunoassay for immunologic phenomena in pneumococcal disease and for the antibody response to pneumococcal vaccines. J. Immunol. Methods 33:133–44.

Sveum, R. J., T. M. Chused, M. M. Frank and E. J. Brown (1986). A quantitative fluorescent method for measurement of bacterial adherence and phagocytosis. J. Immunol. Methods 90:257–64.

Vioarsson, G., I. Jonsdottir, S. Jonsson, and H. Valdimarsson (1994). Opsonization and antibodies to capsular and cell wall polysaccharides of *Streptococcus pneumoniae*. J. Infect. Dis. 170:592–99.

Wenger, J. D., S. R. Steiner, S. B. Pais, J. C. Butler, B. Perkins, G. M. Carlone, and C. V. Broome, (1996). Laboratory correlates for protective efficacy of pneumococcal vaccines: how can they be identified and validated? Abstr. G37 in Program and abstracts of the 36$^{th}$ Interscience Conference on Antimicrobial Agents and Chemotherapy.

Wilkelstein, J. A., M. R. Smith, and H. S. Shin (1975). The role of C3 as an opsonin in the early stages of infection. Proc. Soc. Exp. Biol. Med. 149:397–401.

What is claimed is:

1. A method of simultaneously detecting a plurality of different functional antibodies against multiple bacterial serotypes comprising:
    (a) combining a sample with a first plurality of different antigens, complement and effector cells, wherein the antigens are differentially labeled,
    (b) incubating the sample to allow for internalization of the antigens by the effector cells, and
    (c) detecting internalized antigens, wherein an increase in detectable label as compared to a control sample indicates the presence of internalized antigens and the functional antibodies against multiple bacterial serotypes.

2. The method of claim 1, wherein each member of the first plurality of different antigens comprises a bacterial molecule from a different serotype of a single bacterial species.

3. The method of claim 2, wherein the bacterial species is *Streptococcus pneumoniae*.

4. The method of claim 2, wherein the bacterial species is *Neisseria meningitidis*.

5. The method of claim 2, wherein the bacterial molecule is an intact bacterium.

6. The method of claim 5, wherein the intact bacterium is not viable.

7. The method of claim 1, wherein the sample is taken from a body fluid or tissue of an individual.

8. The method of claim 7, wherein the individual has been immunized with a second plurality of different antigens, wherein the second plurality of different antigens are not labeled but are otherwise the same as the first plurality of antigens.

9. The method of claim 8, wherein the detection of the functional antibody indicates the efficacy of the immunization.

10. The method of claim 1, wherein the complement comprises freeze dried baby rabbit serum.

11. The method of claim 1, the internalized antigens are detected with a flow cytometer.

12. The method of claim 1, wherein the effector cells are macrophages, mononuclear phagocytes, natural killer cells, or granulocytes.

13. The method of claim 1, wherein the effector cells are obtained from the serum of an individual or from an in vitro culture.

14. The method of claim 1, wherein the effector cells are human promyelocytic leukemia cells.

15. The method of claim 1, wherein the antigens are differentially labeled by a plurality of different fluorescent molecules, and wherein an increase in fluorescence as compared to a control sample indicates the presence of internalized antigens and the functional antibodies against multiple bacterial serotypes.

16. The method of claim 15, wherein each member of the plurality of different fluorescent molecules differs from each other member of the plurality in its fluorescence emission wavelength.

17. The method of claim 15, wherein each member of the plurality of different fluorescent molecules differs from each other member of the plurality in its fluorescence intensity.

18. A method of simultaneously detecting a plurality of different functional antibodies against multiple bacterial serotypes comprising:
  (a) combining a sample with a first plurality of different antigens, complement and effector cells, wherein the first plurality of different antigens are attached to different labeled beads,
  (b) incubating the sample to allow for internalization of the labeled beads by the effector cells, and
  (c) detecting the internalized beads, wherein an increase in detectable label as compared to a control sample indicates the presence of internalized beads and functional antibodies against multiple bacterial serotypes.

19. The method of claim 18, wherein the antigens are attached to different fluorescently labeled beads, and wherein an increase in fluorescence as compared to a control sample indicates the presence of internalized beads and the functional antibodies against multiple bacterial serotypes.

20. The method of claim 19, wherein each member of the plurality of different antigens attached to different fluorescently labeled beads differs from each other member of the plurality in its fluorescence emission wavelength.

21. The method of claim 19, wherein each member of the plurality of different antigens attached to different fluorescently labeled beads differs from each other member of the plurality in its fluorescence intensity.

22. The method of claim 18, wherein each member of the first plurality of different antigens comprises a bacterial molecule from a different serotype of a single bacterial species.

23. The method of claim 22, wherein the bacterial species is *Streptococcus pneumoniae*.

24. The method of claim 22, wherein the bacterial species is *Neisseria meningitidis*.

25. The method of claim 18, wherein the sample is taken from a body fluid or tissue of an individual.

26. The method of claim 25, wherein the individual has been immunized with a second plurality of different antigens, wherein the second plurality of different antigens are not attached to different labeled beads but are otherwise the same as the first plurality of antigens.

27. The method of claim 26, wherein the detection of the functional antibody indicates the efficacy of the immunization.

28. The method of claim 18, the internalized antigens are detected with a flow cytometer.

29. A method of simultaneously detecting a plurality of different functional antibodies against multiple bacterial serotypes comprising:
  (a) combining a sample with a first plurality of different antigens, complement and effector cells, wherein the antigens are differentially labeled,
  (b) incubating the sample to allow for internalization of the antigens by the effector cells, and
  (c) detecting internalized antigens using a hematology unit, wherein a change in volume, conductivity, or scatter as compared to a control sample indicates the presence of internalized antigens and the functional antibodies against multiple bacterial serotypes.

30. The method of claim 29, wherein the antigens are differentially labeled by a plurality of different fluorescent molecules.

31. A method of simultaneously detecting a plurality of different functional antibodies against multiple bacterial serotypes comprising:
  (a) combining a sample with a first plurality of different antigens, complement and effector cells, wherein the first plurality of different antigens are attached to different labeled beads,
  (b) incubating the sample to allow for internalization of the labeled beads by the effector cells, and
  (c) detecting the internalized beads using a particle concentration immunofluorescent analyzer, wherein an increase in detectable label as compared to a control sample indicates the presence of internalized beads and functional antibodies against multiple bacterial serotypes.

32. The method of claim 31, wherein the antigens are attached to different fluorescent labeled beads, and wherein an increase in fluorescence as compared to a control sample indicates the presence of internalized beads and the functional antibodies against multiple bacterial serotypes.

33. A method of simultaneously detecting a plurality of different functional antibodies against multiple bacterial serotypes comprising:
  (a) combining a sample with a first plurality of different antigens, freeze-dried baby rabbit serum, and human promyelocytic leukemia cells, wherein the antigens are differentially labeled by a plurality of different fluorescent molecules;
  (b) incubating the sample to allow for internalization of the antigens by the cells; and
  (c) detecting internalized antigens using a flow cytometer, wherein an increase in fluorescence as compared to a control sample indicates the presence of internalized antigens and the functional antibodies against multiple bacterial serotypes.

* * * * *

UNITED STATES PATENT AND TRADEMARK OFFICE
CERTIFICATE OF CORRECTION

PATENT NO. : 6,815,172 B1
DATED : November 9, 2004
INVENTOR(S) : Martinez et al.

It is certified that error appears in the above-identified patent and that said Letters Patent is hereby corrected as shown below:

Column 3,
Line 2, "fictional" should be -- functional --.

Column 8,
Line 36, "20% o" should be -- 20% --.
Line 44, a period -- . -- should be inserted after "flask" and before "The".

Column 9,
Line 2, a period -- . -- should be inserted after "flask" and before "The".

Column 11,
Line 18, an open parenthesis -- ( -- should be inserted before "prepared".

Column 13,
Line 27, a period -- . -- should be inserted after "stock" and before "Adequate".

Column 15,
Line 22, the upper case "L" should be a lower case -- l --.
Line 59, "minima" should be -- minimal --.

Column 16,
Line 41, a period -- . -- should be inserted after "test" and before "A".
Line 44, a comma -- , -- should be added after "0.96" and after "0.90".

Column 18,
Line 19, a period -- . -- should be added after "applications".
Line 38, "s" should be -- as --.
Line 39, a period -- . -- should be added after "FL3".
Line 44, a period -- . -- should be added after "(2%)".
Line 59, a period -- . -- should be added after "mixture".
Line 60, a period -- . -- should be added after "minutes".
Line 66, "K2CO3" should be -- $K_2CO_3$. --.

Column 19,
Line 9, a period -- . -- should be added after "water".
Line 48, "in" should be deleted.
Line 55, "1." should be -- 2. --.
Line 56, a period -- . -- should be added after "hour".
Line 57, "2." should be -- 3. --.

UNITED STATES PATENT AND TRADEMARK OFFICE
CERTIFICATE OF CORRECTION

PATENT NO. : 6,815,172 B1
DATED : November 9, 2004
INVENTOR(S) : Martinez et al.

It is certified that error appears in the above-identified patent and that said Letters Patent is hereby corrected as shown below:

Column 21,
Line 6, "and or" should be -- and/or --.

Column 22,
Line 66, -- wherein -- should be inserted after "claim 1," and before "the".

Column 24,
Line 6, -- wherein -- should be inserted after "claim 18," and before "the".

Signed and Sealed this

Twenty-first Day of February, 2006

JON W. DUDAS
*Director of the United States Patent and Trademark Office*